United States Patent [19]
Lee

[11] 4,034,474
[45] July 12, 1977

[54] JAW MOVEMENT SIMULATION

[76] Inventor: Robert L. Lee, 22937 Grand Terrace Road, Colton, Calif. 92324

[21] Appl. No.: 485,158

[22] Filed: July 1, 1974

[51] Int. Cl.² .......................................... A61C 9/00
[52] U.S. Cl. ................................................ 32/20
[58] Field of Search ...................... 32/19, 20, 21, 32

[56] References Cited

U.S. PATENT DOCUMENTS

| | | | |
|---|---|---|---|
| 1,080,809 | 12/1913 | Burch | 32/19 |
| 2,814,876 | 12/1957 | Stuart | 32/19 |
| 2,818,646 | 1/1958 | Stuart | 32/20 |
| 3,035,348 | 5/1962 | Page | 32/20 |
| 3,694,919 | 10/1972 | Lee | 32/32 |

*Primary Examiner*—Robert Peshock
*Attorney, Agent, or Firm*—Knobbe, Martens, Olson, Hubbard & Bear

[57] ABSTRACT

An upper frame including parallel side arms is supported on the patient's ears and attached to a transverse rod supported on the bridge of the patient's nose. A record plate depends from each side arm overlying each of the patient's temporomandibular joints. A lower frame is attached to the lower jaw by means of an adjustable clutch. Adjustable side arms carrying movable styluses engage the record plates on the upper frame. Movement of the styluses over the record plates is monitored to obtain measurements of the joint movements. A tooth separator swingably mounted on the transverse rod of the lower frame separates the rear teeth slightly when the jaw movements are being measured. After the hinge axis position has been located on the record plates, an adjustable straight edge is utilized to indicate the true horizontal plane of reference formed by the two hinge axis points and the point on the patient's nose. The stylus movements can be monitored mechanically or electronically and the resulting measurements utilized to set an adjustable dental articulator or to select preformed motion analogue blocks having pathways for guiding the styluses of an articulator.

34 Claims, 32 Drawing Figures

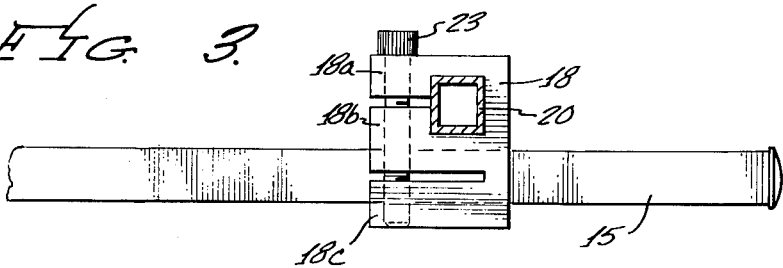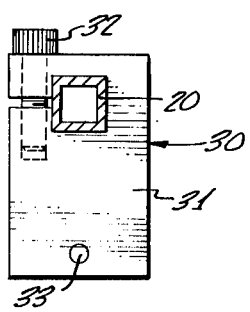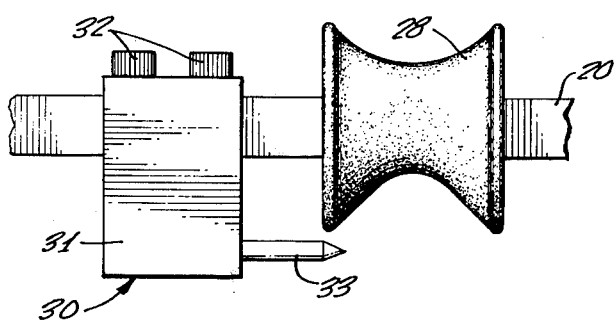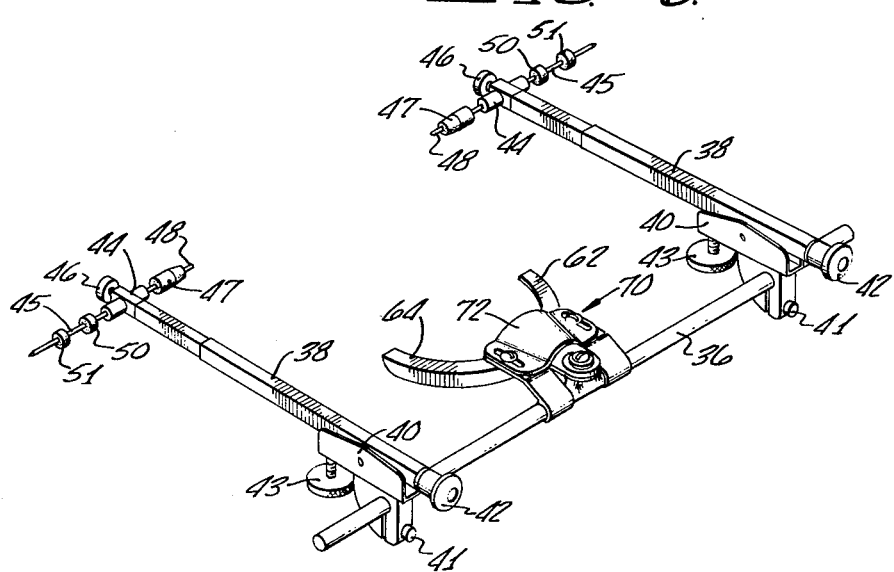

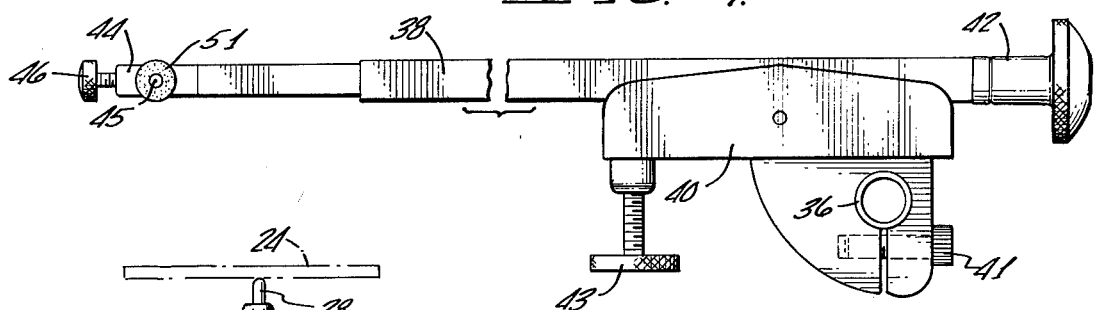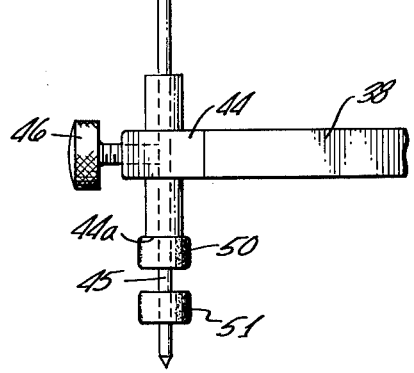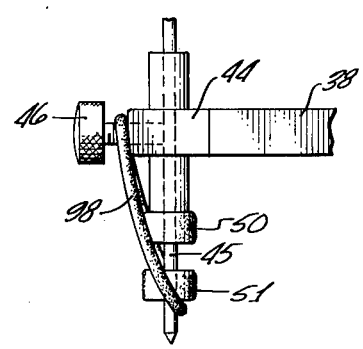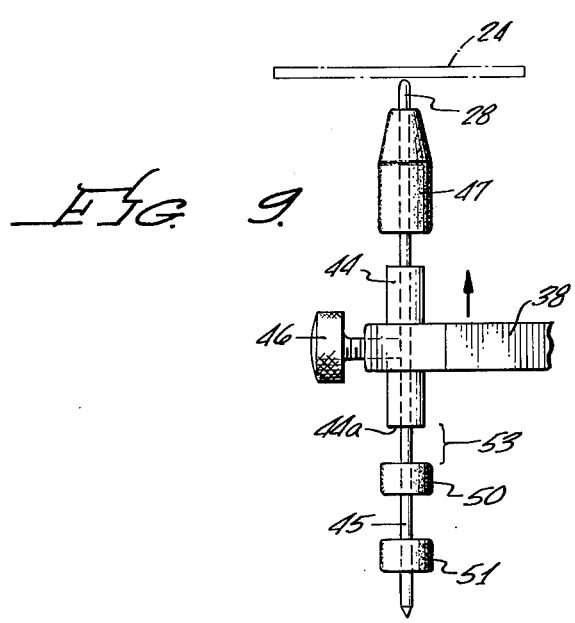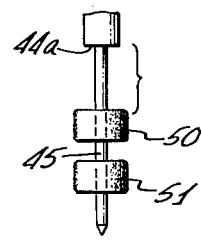

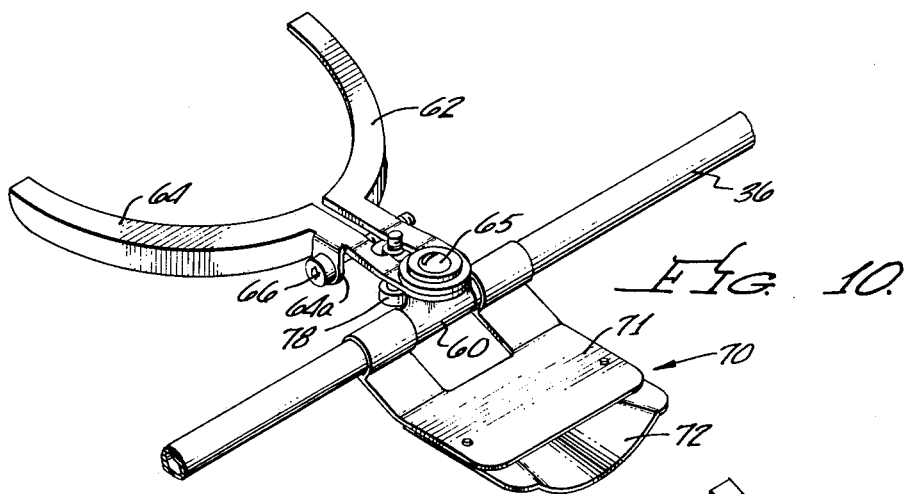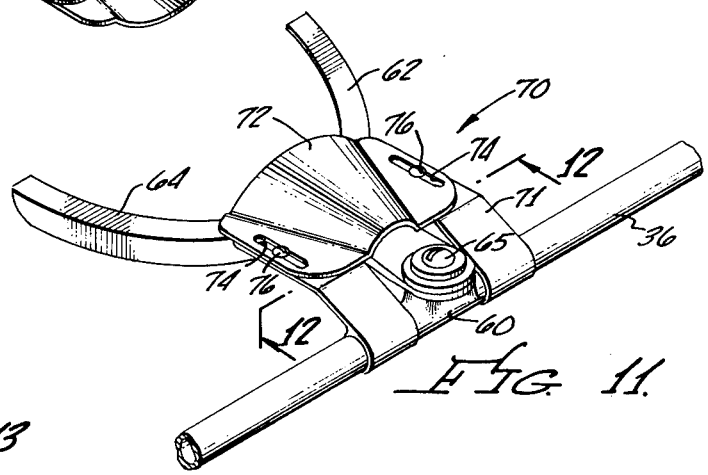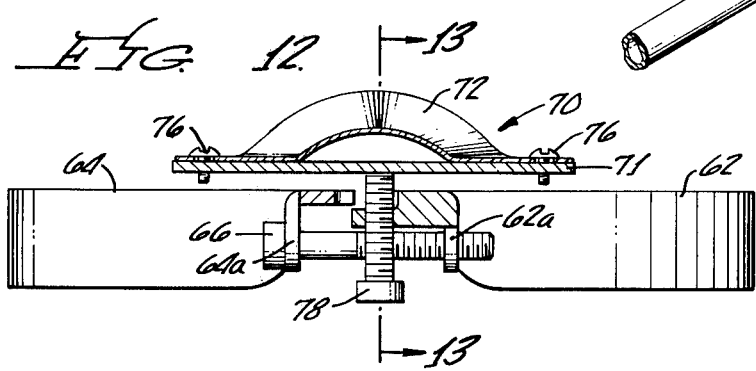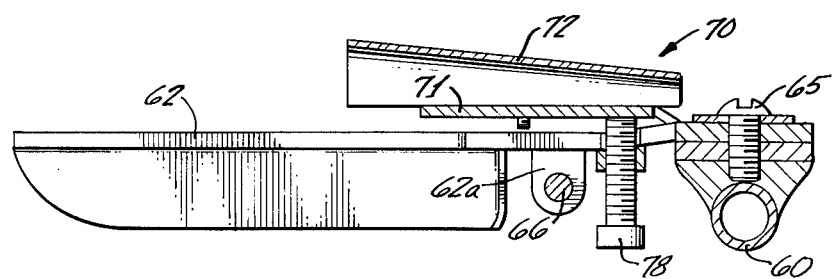

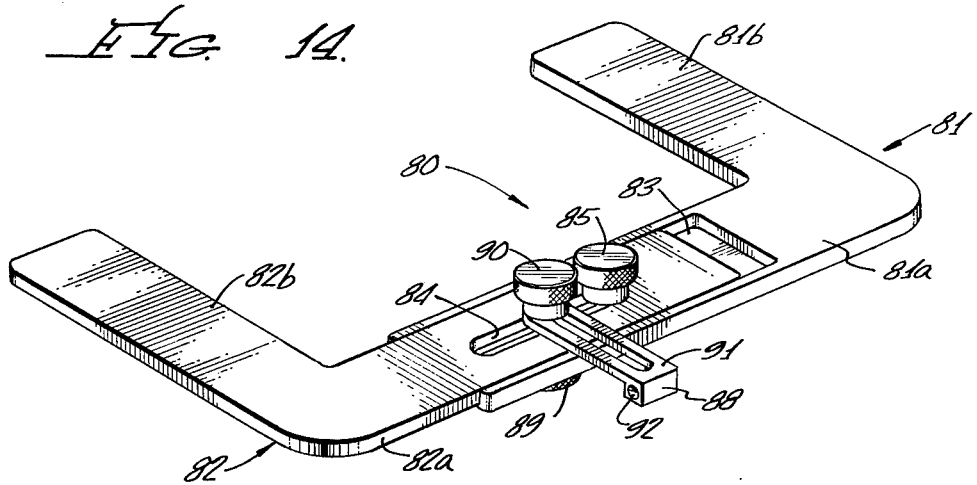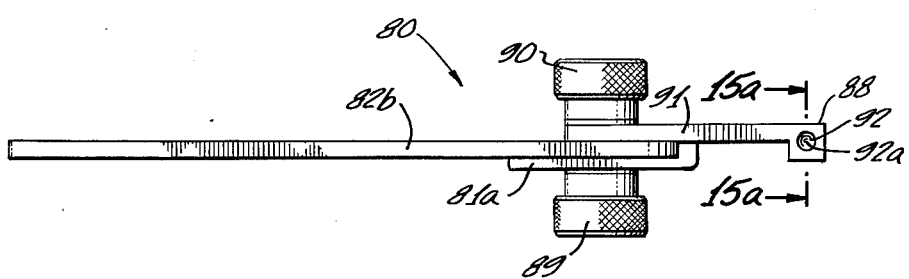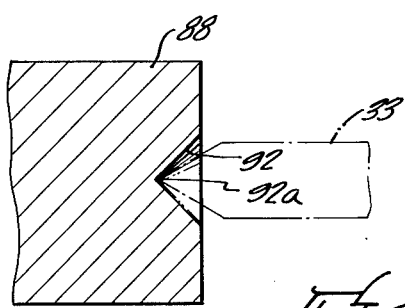

| IMMEDIATE SIDE SHIFT IN mm. | DEGREE OF SLOPE OF PROTRUSIVE PATH | DEGREE OF HORIZONTAL SLOPE OF BORDER PATH | FULL SIDE SHIFT IN mm AT 10mm FORWARD OF CENTRIC POSITION |
|---|---|---|---|
| 0mm | 30° | 45° | 5 / 7 |
| | | 60° | 5 / 7 |
| | 45° | 45° | 5 / 7 |
| | | 60° | 5 / 7 |
| | 60° | 45° | 5 / 7 |
| | | 60° | 5 / 7 |
| 1mm | 30° | 45° | 5 / 7 |
| | | 60° | 5 / 7 |
| | 45° | 45° | 5 / 7 |
| | | 60° | 5 / 7 |
| | 60° | 45° | 5 / 7 |
| | | 60° | 5 / 7 |
| 2mm | 30° | 45° | 5 / 7 |
| | | 60° | 5 / 7 |
| | 45° | 45° | 5 / 7 |
| | | 60° | 5 / 7 |
| | 60° | 45° | 5 / 7 |
| | | 60° | 5 / 7 |

JAW MOVEMENT SIMULATION

This invention relates to jaw movement simulation and more particularly to improvements in apparatus for recording or analyzing jaw movements and the methods of utilizing such apparatus to measure jaw movements. The invention further relates to a system for obtaining simulated jaw joint action for use in a dental articulator by utilizing the jaw movement measurements obtained through the use of the apparatus.

In the making of dental prostheses and in the analyzing and treatment of other jaw disorders, it is desirable to have means for simulating the individual patient's jaw movements. Consequently, a variety of dental articulators have been developed for such purposes. While these are useful instruments with varying degrees of accuracy of simulation, they all only provide fairly rough approximations of the patient's actual temporomandibular joints. The shortcomings of these devices in this regard are discussed extensively in U.S. pat. No. 3,452,439, issued to Robert L. Lee, the same inventor as the present invention. In this patent there is disclosed a system for much more accurately simulating if not actually duplicating a patient's jaw movements. Briefly, the system disclosed therein records jaw movements in solid plastic record blocks. The information stored in these blocks is then transferred by transfer apparatus to prepare a second set of plastic blocks in which are formed guide pathway openings which closely simulate or duplicate the patient's jaw joint movements. These "analogue" blocks are then mounted in a dental articulator to simulate the patient's jaw movements. The walls of the openings in these analogue blocks are three-dimensional and control movement in the 6° of freedom.

While the system disclosed in the aforementioned Lee patent is highly accurate and therefore a very significant contribution to this field, it is relatively costly to obtain a set of analogue blocks through this system. There are many steps to follow in the procedure which take considerable time and skill such that normally the work must be done by a dentist, whoe requires considerable training to become adept at the procedure. In effect, it is a very precise and personalized procedure to obtain a set of custom-made guide blocks for reproducing jaw movements. Consequently, the system has not been widely used being largely limited to research and larger dental schools in that the cost and complexity is more than the usual dentist can justify, and more costly than the patient is willing or capable of paying. Therefore, a need exists for simplifying and reducing the cost of obtaining jaw movements while still maintaining acceptable accuracy.

The present invention accomplishes this by introducing several improvements in apparatus and the method of utilizing this apparatus and other available equipment. As one step in the procedure, it is necessary that certain information regarding the patient's jaw movements be obtained and such information should be obtained relatively quickly and easily and yet accurately. Thus there is provided improved apparatus including a maxillary frame having a pair of side arms with a rigid recording plate perpendicularly mounted on each of the arms to be positioned over the hinge axis of the patient's temporomandibular joints. Also provided is a lower frame which is fixed to the patient's mandible and which has a stylus or transducer probe mounted to engage each of the two recording plates on the maxillary frame to monitor or record mandibular movements.

By utilizing a pair of writing elements as styluses for engaging a paper grid on the recording plates, a curve or line may be traced directly on the grids when the patient's mandible moves from centric relation position to a protrusive position. From this recorded curve various information may be obtained relating to the configuration of the movement of the jaw joints. For example, one important parameter which can be measured is the slope of descent with respect to a horizontal plane of reference. This horizontal reference plane is formed from a point on the nose and the hinge axis line in centric relation position. By means of a special adjustable straight edge tool mounted on the upper frame, the horizontal reference plane may be scribed on the two vertical record plates. The angles can be measured with a suitable tool such as a protractor.

If greater accuracy is desired, the writing element may be replaced by a suitable transducer probe which will monitor the movement electronically wherein the information can be recorded in a variety of fashions or can be shown on a suitable display or other readout device. For example, a current inducing probe may be moved over a grid of electrical wires embedded in the record plate to obtain a readout of the protrusive movement of the probe over the wires. The probe referred to above may be spring mounted in a holder so that movement of the probe in the holder is measured through photoelectric means to obtain a readout of the side shift when the mandible is in a side border movement.

Another parameter of condyle movements relative to the upper jaw is the side shift. This includes both the so-called immediate side shift, progressive side shift and total side shift. Such information is obtained by a displacement technique involving the lower frame apparatus. The styluses on the lower frame which engage the grids on the upper frame are movably mounted on the side arms of the lower frame. Thus these styluses may be slid into engagement with the grids when the patient's mandible is in centric position and the styluses locked in such position. A suitable marker is mounted on the outer end of the stylus with its inner or medial side in engagement with the structure supporting the stylus, or other suitable reference surface. The styluses are then unlocked and the patient's mandible is moved to one side (as in chewing) to the extent possible to demonstrate any immediate side shift of the condyles. This motion will cause the stylus mountings on the side opposite to the direction the jaw moves to slide inwardly on its stylus because the stylus inner end is in engagement with the stationary grid on the upper frame apparatus. The marker on the stylus becomes correspondingly spaced from the reference surface. Thus it is a simple matter to measure the distance between the reference surface and the marker, which represents the displacement of the stylus and the condylar side shift. The characteristics of the side shift timing can also be observed as to wehter the side shift is immediate, progressive, nonprogressive, or both immediate and progressive, or does not exist at all.

Again, these measurements may be performed entirely mechanically and manually or they may be monitored and measured electronically.

While measuring these jaw movements, it is important that the patient's teeth not restrict the full range of movement so that the characteristics of the joints may be determined as accurately as possible. Further it is particularly important that the patient's mandible be easily and repeatedly movable into centric relation position. Hence the patient's rear teeth should be slightly separated during such movement. The prior art discloses a rather cumbersome procedure for obtaining such separation which involves fabricating clutches for both the mandible and maxilla. The present invention employs a simplified tooth separator which is mounted on the lower frame in a manner such that the patient's upper front teeth or ridges can simply rest on the separator. Also the separator is conveniently mounted to be quickly moved out of the patient's mouth so that the operator can easily place or remove the clutch from the teeth. The separator is adjustable in several respects to accommodate various jaw sizes and relationships.

More specifically, the tooth separator is pivotally mounted on a transverse rod on the lower frame which is the same rod supporting the side arms of the frame. The frame is attached to the patient's lower jaw by means of an adjustable clutch mounted on a strut which in turn is connected to the transverse rod. An adjustable screw extends through the strut and engages a lower surface on the tooth separator to provide vertical adjustment for the separator.

The information obtained by utilizing the above described apparatus and methods can be employed for adjusting various dental articulators and thus the apparatus and methods are useful just for that reason alone. The information may also be used with the more accurate preformed analogue guide blocks described above in connection with the aforementioned Lee patent. With the system of the Lee patent analogue blocks simulating the joint motions of patients have been accumulated for a large number of patients representing a considerable cross section of jaw joint anatomy and physiology. The information obtained from this large group of actual patients has been analyzed and it has been discovered that while all such analogue blocks are different, nevertheless the joint movements of patients have certain similar characteristics. By classifying these characteristics on the basis of parameters of jaw movements which can be measured by the apparatus described above, it has been found that they fall into a statistical normal curve distribution. Therefore, most of these patients can be logically classified into a relatively small number of groups so that analogue blocks made in accordance with the average values of the patients in a particular group of these readily measurable parameters will provide a reasonable approximation of the patient's condyle movements. These approximations are much more accurate than that which can be obtained through the use of the typical articulator. Since a patient can be so catagorized or classified, a group of standarized or average value blocks may be made by inexpensive plastic molding techniques and a supply or inventory of such standard sizes can be made available at a relatively modest cost. Thus the individual dentist may make the various necessary jaw measurements utilizing the apparatus and methods described above, and then simply select the set of preformed analogue guide blocks which most closely approximate his patient's jaw motions. These blocks are then mounted in a standard dental articulator and used to simulate that patient's jaw movements. By the use of the system the average dental practitioner can provide more precise or individualized treatment at a reasonable cost.

Further features and advantages of the invention will be apparent by reference to the following detailed description and drawings in which:

FIG. 3 is a cross-sectional view taken along the lines 3—3 of FIG. 2 to illustrate the mounting of the transverse rod of the upper frame with respect to the side arms;

FIG. 4 is a cross-sectional view on lines 4—4 of FIG. 2 illustrating the mounting of the nose pointer;

FIG. 5 is a front elevational view of the nose pointer;

FIG. 6 is a perspective view of the lower frame apparatus;

FIG. 7 is a side elevational view of the lower frame apparatus;

FIG. 8 is a plan view of one of the styluses of the lower frame in engagement with the record plate of the upper frame with the side movement marker in its initial position;

FIG. 8a is a view like FIG. 8 with the stylus being urged against the record plate by an elastic band;

FIG. 9 is a view like FIG. 8 after the lower frame except the stylus holder has been shifted sideways on the stylus away from its marker in response to immediate side movement of the patient's mandible;

FIG. 9a is a fragmentary view of FIG. 9 showing the displacement for full side shift;

FIG. 10 is an enlarged perspective view of the tooth separator of the lower frame with the separator in the position is occupies outside of the patient's mouth;

FIG. 11 illustrates the tooth separator in its operating position;

FIG. 12 is a cross-sectional view of the separator on lines 12—12 of FIG. 11 illustrating the vertical adjustment of the separator;

FIG. 13 is a side cross-sectional view on lines 13—13 of FIG. 12 further illustrating the configuration of the separator;

FIG. 14 is a top perspective view of a tool for locating the exact horizontal plane of reference formed by the jaw hinge axis and a point on the patient's nose;

FIG. 15 is a side elevational view of the tool of FIG. 14;

FIG. 15a is a cross-sectional view of the dimple of FIG. 15;

UPPER HEAD FRAME

Figure 1:
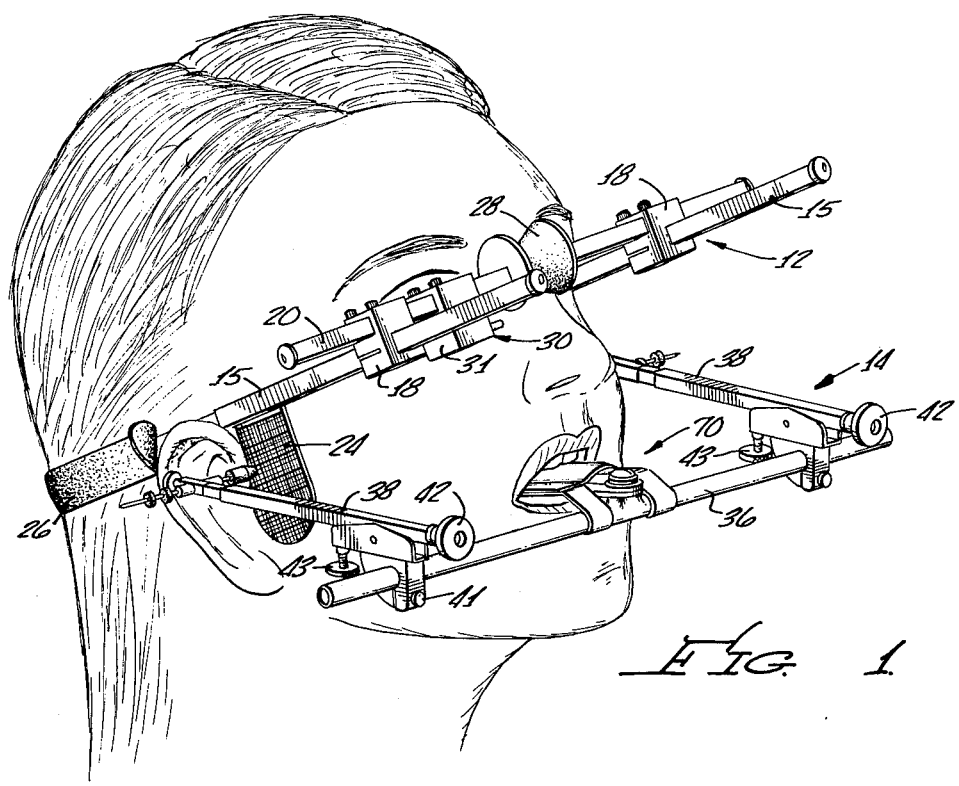
FIG. 1 is a perspective view illustrating the apparatus of the invention mounted on a patient.
Figure 2:
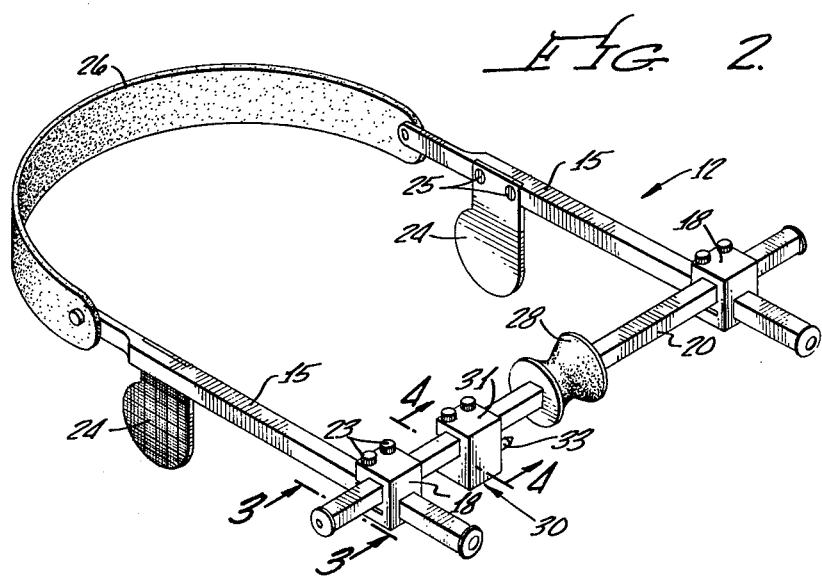
FIG. 2 is a perspective view of the upper frame apparatus.

Referring first to FIG. 1 there is shown an upper frame 12 and a lower frame 14 mounted on a patient's head 10. As can be seen the upper frame is mounted on the patient's nose and ears, while the lower frame is attached to the patient's lower jaw. Referring to FIG. 2, it may be seen that the upper frame apparatus includes a pair of side arms 15 formed of rigid materials such as metal or plastic and having a square cross-section. The side arms 15 are slidably mounted in support blocks 18. A transverse rod 20 is also slidably mounted in the support block 18 in perpendicular relation to the side arms 15. As can be seen from FIG. 3, the transverse rod 20 also has a square cross-section so that it is permanently held in perpendicular relation to the side arms even though the side arms may be moved forwardly and rearwardly to be suitably adjusted on the patient's ears and may be moved sideways to fit the width of the patient's head. Suitable clamping screws 22 and 23 extend through the block 18 to lock the side arms in a selected position. More specifically, the outer screw 22 clamps the upper and middle segment 18a and 18b (FIG. 3) of the clamp 18 to fix the side arms laterally with respect to the transverse rod 20 while the inner screw 23 clamps the upper and lower segments 18a and 18c to fix the rearward or forward movement of the side arms with respect to the transverse rod.

A stiff or rigid reference or recording plate 24 is attached to each of the side arms 15 adjacent the rear end of the arms by a pair of screws 25 or other suitable means. The plates are mounted in fixed perpendicular relation with respect to the arms 15 and 16 and extend downwardly to be positioned in front of the patient's ears as seen in FIG. 1. Each plate has a curved lower portion which extends rearwardly towards the ear so that the plate completely covers the area of the patient's temporomandibular joint when mounted on the patient's face as seen in FIG. 1. On the other surface of each plate is a grid of intersecting lines which are perpendicular to each other, and therefore the vertical lines are perpendicular to the side arms 15 and 16 and the horizontal lines are parallel to the side arms. The grid may conveniently be formed on a separate sheet of paper held by adhesive to the plate in a manner such that the sheet is readily removed from the plate. A flexible strap 26 attached to the rear end of the side arms helps maintain the upper frame on the patient's head.

Mounted on the center of the transverse rod 20 is a nasion support 28 which rests on the bridge or nasion of the patient's nose. As can be seen from FIG. 5, the support 28 has a smoothly curved central section tapering to larger diamger flanges on the ends. The curvature of the support is not symmetrical and it may be rotated on the support 20 to best to conform to the patient's nasion.

Also mounted on the transverse rod 20 is a pointer assembly 30 comprising a mounting block 31 which is slidably mounted on the transverse rod 20. The mounting block 31 may be locked in a desired position by means of the screw 32 attached. A pointer 33 is mounted on the lower end of the block 31 extending generally parallel to the rod 20 towards the support 28. With this arrangement, it may be seen that the pointer is transversely adjustable on the rod 20 but remains fixed a preselected distance below the transverse rod 20 and parallel to the rod.

LOWER HEAD FRAME

Referring to FIG. 6, it may be seen that the lower head frame 14 includes a transverse rod 36 on which is mounted a pair of side arms 38. The side arms are each attached to the transverse rod 36 by a supporting unit 40 which keeps the side arms perpendicular to the transverse rod 36 while permitting them to be individually slid transversely on the rod and locked by means of a screw 41; individually moved rearwardly and forwardly by means of the adjusting screw 43; and moved angularly with respect to the transverse rod 36 by means of the adjusting screw 43 all as seen in FIGS. 6 and 7.

Positioned on the end of each of the side arms 38 is a tubular holder 44 which extends perpendicular to the side arm parallel to the transverse rod 20. A stylus, or axis pin, or other small diameter element 45 is slidably positioned in the tubular holder 44. A set screw 46 threads into the interior of the holder to lock the stylus in its desired position. On the inner end of the stylus 42 is mounted another tubular holder 46 in which is firmly positioned a scribe or writing element 48. The scribe 48 may be forcefully removed and replaced by another element or transducer. The entire stylus can be a writing element is desired.

On the other end of the stylus 45 is slidably mounted a ring shaped marker 50 which is made of teflon, plastic or other suitable material which will grip the stylus 45 but yet may be manually slid on the stylus.

CLUTCH AND TOOTH SEPARATOR

Referring to FIGS. 10–13, a T-shaped support member 60 is mounted between two halves of the transverse rod 36. A pair of clutch pieces 62 and 64 are attached to the support 60 by means of a screw 65. As can be seen, each of the clutch pieces 62 and 64 includes strut position whose forward end is attached to the support 60 and whose rearward end supports a curved portion adapted to fit over the lower teeth or gums of the patient. Each of the clutch strut portions includes a depending flange 62a and 64a. An adjusting screw 66 is threadedly mounted in the flanges so that the spacing between the clutch pieces 62 and 64 is laterally adjustable by means of the screw 66.

Pivotally mounted on the transverse rod 36 is a tooth separator 70. More specifically, the separator 70 includes a base plate 71 having a pair of arms straddling the clutch support member 60 and which fit over the transverse rod 36 so that the base plate is swingable about the rod. The base plate 71 further includes a flat portion on which is mounted a separator or contact element 72. The separator element has a pair of side flanges with elongated mounting slots 74 which receive screws 76 threaded into the separator base plate 71. This arrangement of course permits front to rear adjustment of the separator elements 72 with respect to the base plate 71. The upper surface of the separator element 72 is smoothly curved into an arch shape from side to side as seen in FIGS. 11 and 12. Also, as seen by FIG. 12, the element 72 slopes downwardly in the forward direction. The patient's upper teeth or gums engage the upper surface of the separator element 72. The height and shape of the arch may be selected to best fit the patient's mouth. Various separator elements may be employed since they are readily separable from the base plate 71.

As may be seen from FIG. 10, the separator may be swung out of operating position, or may be positioned in operating position as shwon in FIG. 11. In this latter position, the base plate 71 is supported by an adjustable screw 78 which is threadedly mounted in the portion of the clutch element 64.

STRAIGHT EDGE TOOL

Referring to FIG. 14, there is shown a straight edge tool 80 to be used with the upper frame for marking the horizontal plane of reference for the jaw movements measured. As can be seen, the tool has a generally U-shaped formed by two L-shaped flat plates 81 and 82. The right plate 81 as shown in FIG. 14 has a recess 83 in its transverse leg 81a which receives the transverse leg 82a of the left plate. The depth of the recess is equal to the thickness of the left plate so that the upper surfaces of the two plates are in the same plane. The recess 83 in the right plate permits lateral adjustment of the plates so as to vary the distance between the rearwardly extending parallel legs 81b and 82b of the plate. To lock the plates at the selected position, there is provided an elongated slot 84 in each of the overlapping legs 81a and 82a of the plates with said slots being aligned so that a bolt 85 extends through the slots and a locking nut 86 is threaded onto the bolt to clamp the plates to each other.

A pointer receiving element 88 is clamped to the tool by means for another nut 89 and bolt 80 combination extending through the slots 84 in the left and right plates. Thus, the element is laterally adjustable by moving the bolt 90 laterally. The element also has an elongated slot 91 formed therein which permits it to be adjustable from front to rear, or angularly. Formed in one edge of a depending lug at the forward end of the element 88 is a dimple 92 for receiving the pointer 33 on the upper frame As can be seen from FIG. 15, the center 92a of the dimple is precisely aligned with the upper surface of the plate of U-shaped tool 80 so that the dimple is in the same plane with the upper surface.

OPERATION

As the first step for utilizing the apparatus of the invention, the lower frame 14 without the side arms 38 is attached to the patient's mandible. The clutch elements 62 and 64 shown in FIG. 10 are laterally adjusted by means of the adjusting screw 66 to fit the patient's lower jaw. The tooth separator 70 should be swung to the position shown in FIG. 10 where it is not in operating position. The lower side of the clutch elements 64 and 62 which extend into the patient's mouth is then filled with a denture compound or plastic. While the compound is still pliable the clutch is inserted into the mouth over the lower teeth so that the compound is pressed onto the buccal surfaces of the teeth. After the compound hardens the clutch may be removed from the teeth. Denture paste is then inserted into the compound and the clutch is reinserted over the lower teeth. After several minutes, the paste will have hardened so that the clutch attached to the transverse rod 36 is securely fixed to the teeth.

The upper frame 21 is now positioned on the patient. The set screws 21 and 22 are loosened so that the apparatus may be positioned over the patient's head. The nasion positioner 28 is rotated to fit the particular shape of the nose. The patient holds the nasion positioner against the nose while the operator moves the side arms 15 and 16 inwardly towards the patient's head and front to back, until the grid plates 24 are positioned just in front of the ears and the side arms fit snuggly against the side of the head. The rear portion of the side arms rest next to the head on top of the ear. The set screws 21 and 22 are now tightened in this position to hold the side arms in fixed relation perpendicular to the transverse rod 20. The elastic strap 26 attached to the ends of the side arms is positioned around the back of the head to help hold the upper frame in proper position.

The pointer 33 which is previously loosened on its mount is moved transversely to engage the patient's nose a predetermined distance below the transverse rod 20, and the pointer is then locked in such position.

The adjustable side arms 38 of the lower frame 14 are now slid onto the lower transverse rod 36 and moved inwardly until the writing elements 48 engage the grid on the recording plates 24. Note that the lateral or outer ends of the scribe holders 47 must be spaced sufficiently from the stylus supports 44 to allow for lateral jaw movements. Four to five millimeters should accommodate any such movement.

As a next step, the patient's hinge axis in centric relation position should be located. The tooth separator 70 is swung inwardly into the patient's mouth so that the patient's upper front teeth or ridge will engage the upper surface of the curved separator element 72 as may be seen in FIG. 14. The patient's mandible is opened and closed while in the terminal hinge position, that is, where the lower jaw is in its most rearward position. It is important that the back teeth be slightly separated in that the muscles of the jaws tend to draw the lower jaw into its rearwardmost position, but the rear teeth could act as a fulcrum and interfere with this action if the upper and lower teeth are not separated. Thus it would be more difficult to keep the lower jaw in its hinge axis position.

As the patient's mandible is moved up and down in the terminal hinge position, the side arms 38 of the lower face bow 14 should be adjusted vertically and from front to back until the writing elements, or scribes 48 no longer arc, but simply rotate. The grid lines on the plates 24 are helpful in this step as they act as references. This is the point where the hinge axis exits from the hand and is the starting point for the recording measurements. Consequently, with the side arms 38 so positioned, the set screws for positioning the side arms are locked so that the scribes 48 are fixed in aligned relation with the patient's hinge axis. This point is illustrated at 93 in FIG. 20.

Figure 20:
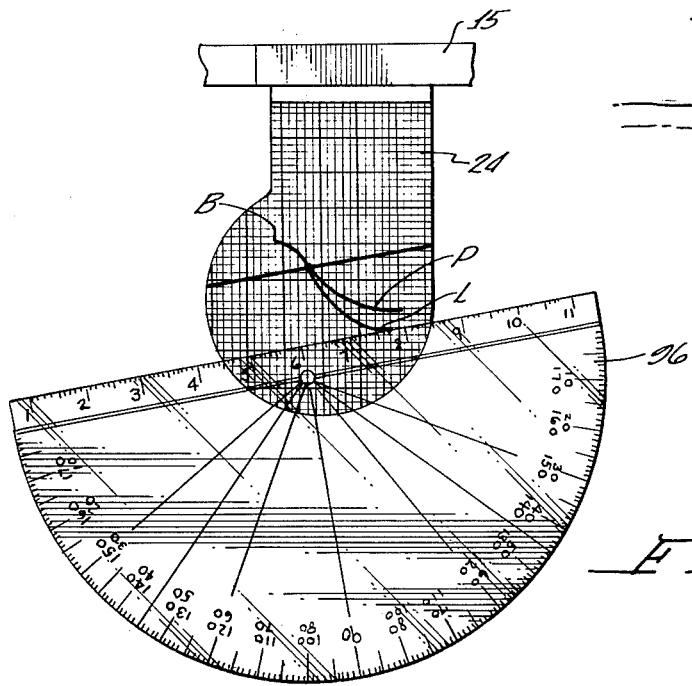
FIG. 20 is an enlarged view of a record plate with the plane of reference and the movement curves marked thereon, and a protractor for measuring the curve angle from this plane.

To measure the protrusive movement, the patient's mandible is placed in the terminal hinge position or centric relation position and the two axis styluses 45 are pushed inwardly so that the scribes 48 are tightly against the grid plates 24. The styluses are then locked with the set screws 46. The patient then protrudes the lower jaw while the two scribes 48 trace a path P of the protrusive movement on the grids. Since the upper wall of the human temporomandibular joint usually slopes downwardly, the patient's condyles will usually move downwardly as they move forward. This is indicated in phantom lines in FIG. 15. Because of movement in this fashion, the path P traced on the grids slopes or curves downwardly as shown in FIG. 20. The slope of this downward and forward curve may be read on a suitable reference line on the grid.

While the angle of protrusive movement may be measured with respect to a horizontal line on the grid which is parallel to the side arms of the upper frame, it is preferable that the angle be measured with respect to the true horizontal plane of reference formed by the terminal hinge axis position and the point which is located on the side of the patient's nose by the pointer 33. This is preferred because this is the reference plane used for mounting denture casts in an articulator.

Figure 16:
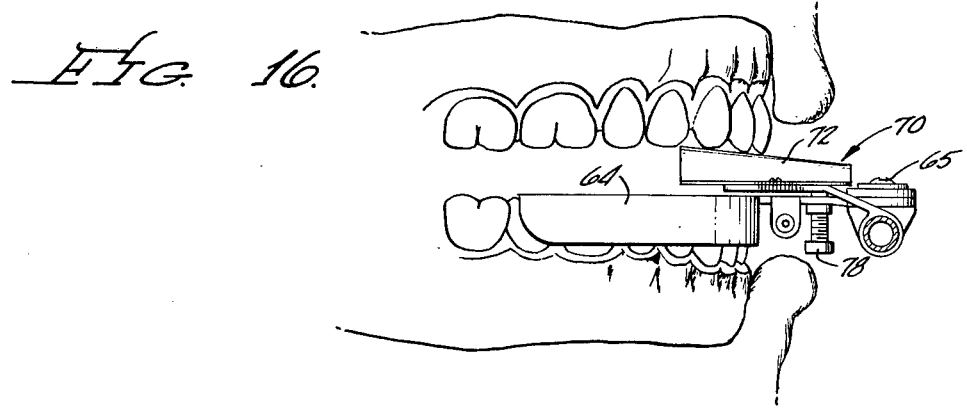
FIG. 16 is a side elevational view of a patient with the tooth separator in use.
Figure 17:
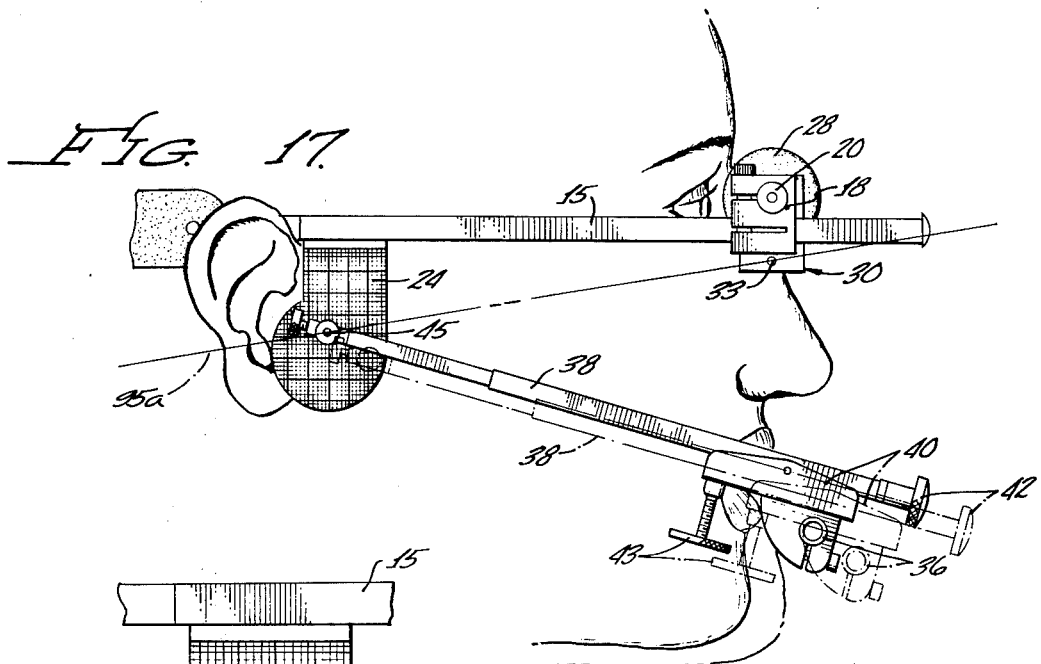
FIG. 17 is a side elevational view of the recording frames in use on the patient's head and with the protrusive movement of the mandible shown in phantom lines.
Figure 18:
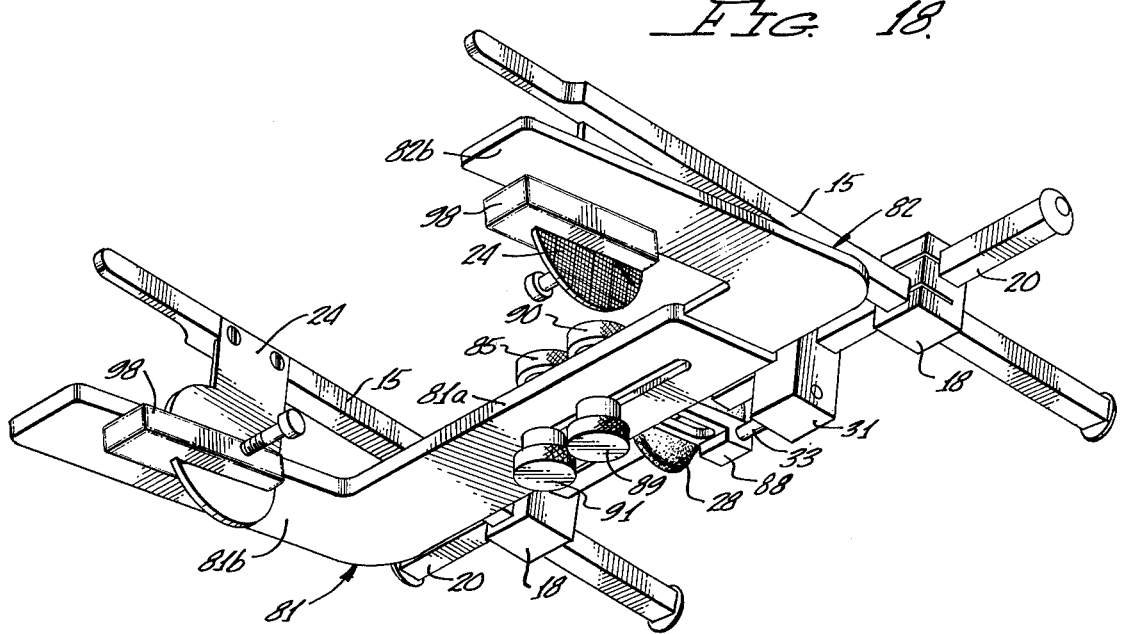
FIG. 18 is a lower perspective view of the horizontal reference plane tool positioned on the upper frame.
Figure 19:
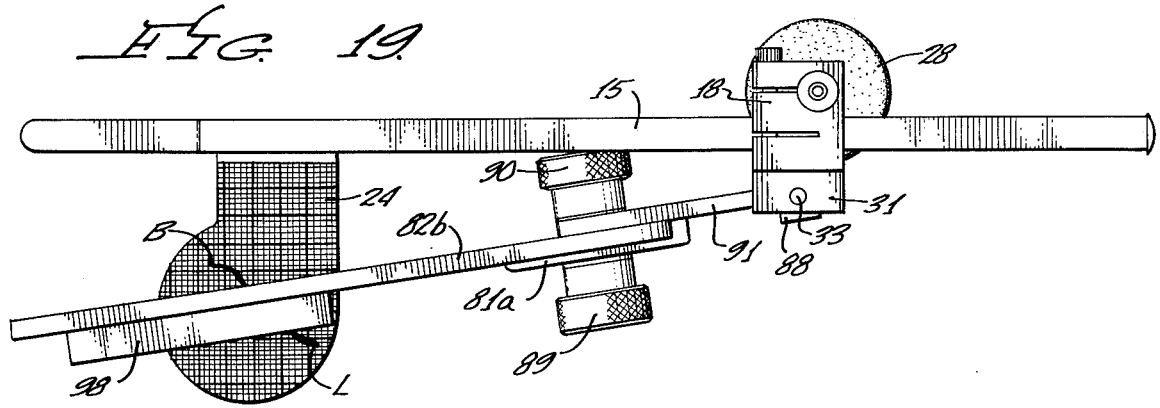
FIG. 19 is a side elevational view of the horizontal reference plane tool on the upper frame.

The reference plane straight edge or tool tool 80 is used to physically mark the plane on the grid paper on the plates 24, as shown in FIGS. 18 and 19. More specifically, after the protrusive and lateral jaw movement curves P and L, FIG. 20, are marked on the grids, the upper frame 12 is removed from the patient and the U-shaped reference plane tool 80 is positioned to straddle the arms 15 and the recording plates 24 on the upper frame. The legs of the U-shaped tool are laterally adjusted so that they just engage the outer sides of the recording plates 24. The pointer 33 is positioned in the dimple 92 formed in the element 88 attached to the reference plane tool, as shown in FIG. 15A. Note that the element 88 can be adjusted laterally and rearwardly to easily receive the pointer. With the forward end of the tool so positioned by the pointer, one leg of the tool is aligned on the recording plate 24 which it engages so that the hinge axis point 93 is in the reference plane forming the upper surface of the tool. The tool is temporarily clamped in this position by a suitable clamp 98 shown in FIG. 16. The other leg of the tool is then similarly positioned on the other recording plate. By using the tool as a straight edge, a line 95 can then easily be drawn on the grid paper on the recording plate through the hinge axis 93 to represent the reference plane, shown as 95a in FIG. 17. Such a reference line 95 can be marked on both the grids. The reference plane tool 80 is then removed so that the protrusive angle can be readily measured with a protractor 96 or other similar tool.

It will be noted that the slope of the protrusive curve P changes. Thus, it can be measured at any number of points as desired or can be constantly monitored. If comparisons are desired between recording plaaes of various patients, a standard measurement point with respect to the hinge axis point 93 can be selected.

Referring to FIGS. 8 and 9, another measurement to make is the side shift or lateral displacement of the condyles when the jaw is moved to one side as in chewing. First, the mandible is placed in centric relation position. Second, the stylus is pushed inwardly until the writing tip touches the recording plate. Third, the adjustable screw 46 is tightened to lock the stylus 45 and the marker 50 is slid inwardly on the stylus 45 until it is engaging the outer or lateral surface 44a of the holder 44, as seen in FIG. 8. Next, the adjustable screw 46 locking the stylus 45 with respect to the holder 44 is loosened on one side of the lower frame. The mandible is then moved directly laterally to the extent possible in the direction to move the side of the lower frame on which the screw 46 has been loosened toward the adjacent recording plate. In other words, referring to FIG. 9, the arm 38 is moved, as indicated by the arrow, toward the recording plate 24. The stylus 45 cannot move in that direction because its inner end 48 is in engagement with the plate 24 on the fixed upper frame. Instead, the holder 44 on the arm 38 slides inwardly on the stylus 45. The marker 50 remains fixed on the stylus 45 and thus the reference surface 44a is spaced from the marker 50. it is a simple matter to measure the displacement 53 of the holder 44 which represents the direct or immediate mandibular side shift in one direction. A similar procedure is followed to obtain the side shift in the other direction.

Also the so-called full mandibular side shift is obtained in this manner but the mandible is allowed to make a more complete side chewing movement. During a full chewing movement, the mandible moves forwardly as well as laterally. The border of this combined movement can be recorded by having the stylus 45 trace the path of the hinge axis motion on the vertical plates simultaneously with the side shift measurement. For this purpose, an elastic or small spring 98 shown schematically in FIG. 8a is employed to urge the stylus against the plate at all times so that a tracing is obtained. The elastic 98 extends between the holder 44 and the outer element 51 tightly mounted on the stylus 45. Referring to FIG. 20, the path L of this full chewing movement usually has a steeper slope than that of the protrusive movement P.

As the hinge axis moves during a side chewing movement producing downward and forward slope on one side of the head as evidenced by the path L, the stylus on the other side of the head representing movement of the other end of the hinge axis is moved upwardly and rearwardly a small amount. This path which is shown on FIG. 20 as B and often referred to as backlash, is caused because the tip of the scribe recording the path is spaced laterally from the condyles within the head.

While the border path of the side chewing movement is being recorded on the grid record plate 24, the complete side displacement is being measured by the markers 50 being displaced relative to the reference surfaces 44a on the holders 44. By returning the mandible back to centric position, the displacement is easily measured. This displacement is shown at 55 in FIG. 9a as typically being considerably greater than the immediate side shift 53 in FIG. 9.

ELECTRONIC MEASURING MEANS

Figure 21:
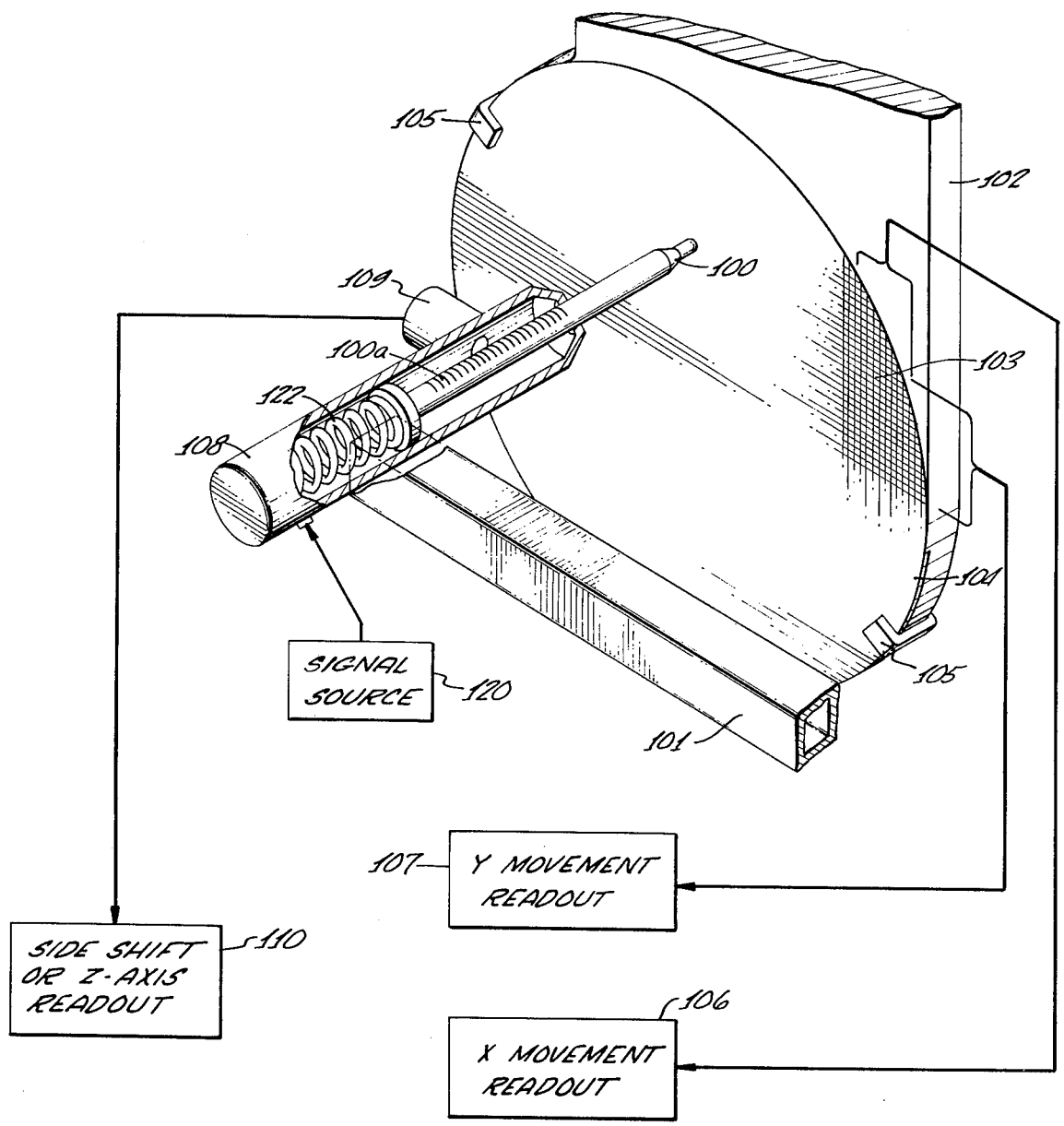
FIG. 21 is a schematic perspective view of apparatus for electronically monitoring jaw movements.

As mentioned above the movement of the styluses 48 may be monitored electronically as well as mechanically. Such an arrangement is schematically illustrated in FIG. 21 wherein the stylus is in the form of a current inducing probe 100 supported on an arm 101 of a lower frame, and connected to a signal source 120. A recording plate 102 attached to the upper frame has a grid 103 of insulated electrical wires embedded in a thin sheet 104 rotatably supported on the surface of the recording plate by three clips 105, which grip the sheet 104 but permit limited rotation in order to align the grid with the true horizontal reference plane. The sheet 104 is transparent on its outer surface so that the wires are visible and can serve as alignment grid lines. Also the sheet is sufficiently self-supporting so it remains flat when supported on its edges in the vertical orientation shown.

As the patient's jaw is moved into protrusive position, the probe 100 is moved adjacent the surface of the sheet 104 inducing current in the grid of wires 103, as the probe crosses a wire. These current signals are sensed and recorded, on suitable readouts, indicating the movement on the surface of the recording plate. In the arrangement shown, the signals produced in crossing the vertical wires, that is, moving horizontally, or in the X axis direction, are displayed on an X-movement readout 106 and the signals resulting from a crossing of the horizontal wires, that is, moving vertically, or in the Y axis direction, are displayed on a Y-movement readout 107. The output may be shown on counters or they may be combined and shown on an oscilloscope type display, if desired. In either event the position of the probe along the surface of the record plate is thereby monitored.

The details of the current inducing probe, the grid, and the readouts are not disclosed herein in that such position identifying devices are prior art. For example, U.S. Pat. Nos. 3,461,454 and 3,647,963 each disclose systems that could be adapted to this purpose. Moreover, there are a variety of digitizers known in the prior art which could be utilized in such an application.

In use, the arm 101 of the lower frame is adjusted until the hinge axis is located, and the arm is then fixed to the transverse rod 36 of the lower face bow. The hinge axis is located when arcuate movement of the probe 100 stops, as indicated by the X and Y readouts 106 and 107, as the mandible is opened and closed. Before protrusive movement is commenced, suitable adjustments may be provided to make the protrusive movement readings measurable with respect to the reference plane 95a defined by the hinge axis and the pointer 33. As one approach, a reference plane tool (not shown) similar to the tool 80 but adapted to be positioned over the upper face bow while the bow is on the patient is then aligned with the probe 100 and the nose pointer 33, FIG. 18. The grid sheet 104 is then rotated so that its horizontal lines are parallel with the planing tool. The plane tool is then removed, the readout set to zero; and protrusive movements commenced. The slope of the protrusive curve can be determined from the readout information on the XY axes of the grid. It should be noted that this method of having the grid sheet rotatable to align the horizontal lines on the grid with the reference plane 95a can also be used in the mechanical arrangement discussed above.

For measuring the side displacement of the lower jaw, or in other words, the movement of the lower frame in the lateral or outward direction, other known plotting arrangements may be employed. For example, the probe 100 is urged against the grid 103 by a spring 122 confined in a holder 108 which supports the probe 100 and is attached to the side arm 101. A transducer unit 109 mounted on the holder 108 adjacent the probe 100 is provided to measure the lateral movement of the holder with respect to the probe. The probe is provided with suitable markings 100a which are monitored or counted by the transducer unit 109. The output of the transducer is transmitted to a suitable Z axis readout 110 for indicating side shift. The transducer 109 is well known in the art, one such arrangement comprising a light source, a small metrological grating, and a photosensitive cell. The output of the photosensitive cell is a series of pulses; each pulse indicates that the holder has moved a predetermined incremental distance. Further details regarding such a sensing arrangement may be found in U.S. Pat. No. 3,434,218. It should be understood that a variety of methods are known for monitoring and measuring such movement electronically. This horizontal or lateral motion, monitored on the so-called Z axis, can be syncronized with the signal from the XY positions so as to give a changing positional reading of the probe tip in relation to the XYZ axis of its starting position. In other words, at any given point in time in a specific jaw movement, the stylus tip position can be determined with respect to the horizontal reference plans by the X, Y, Z coordinates.

USE OF JAW MOVEMENT INFORMATION a. Jaw Movement Simulators

Figure 22:
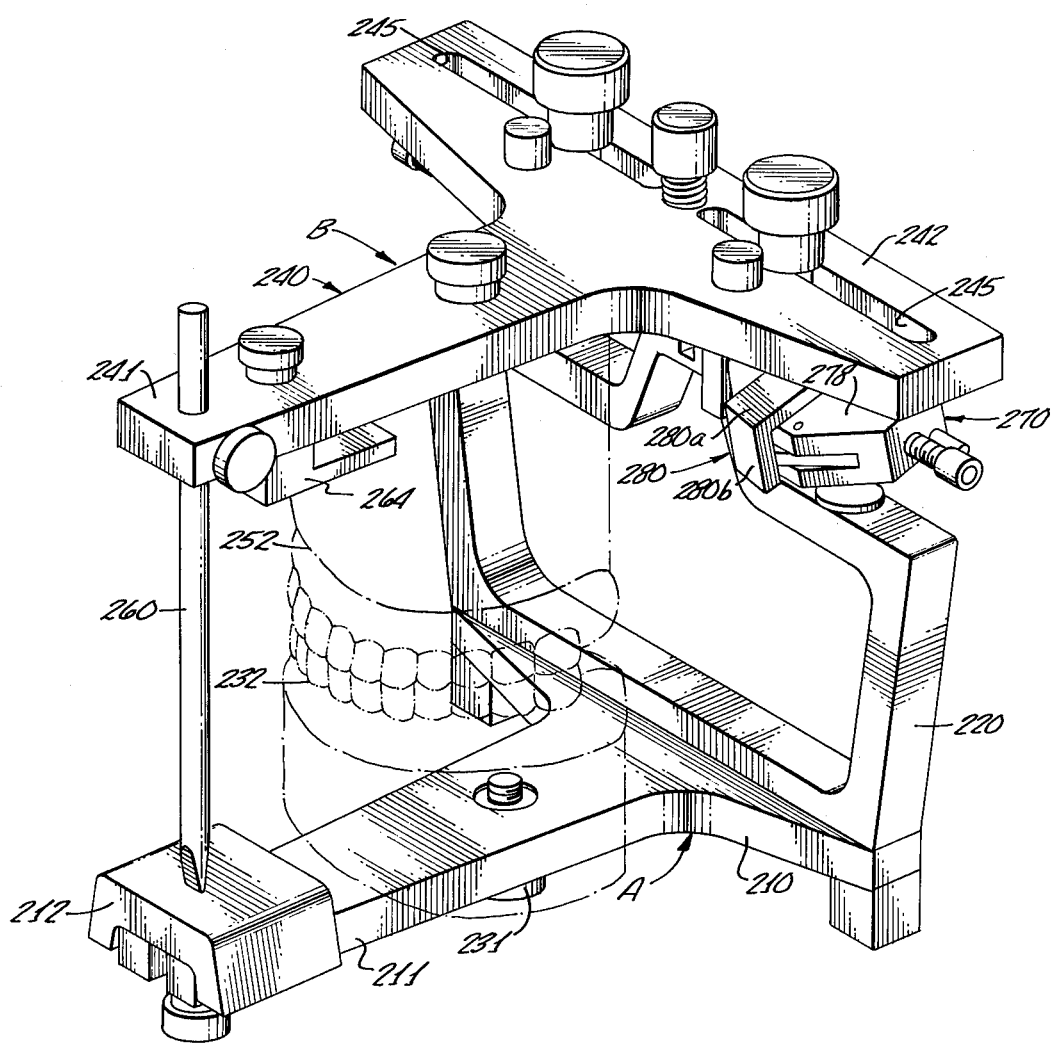
FIG. 22 is a perspective view of a jaw movement simulator.
Figure 23:
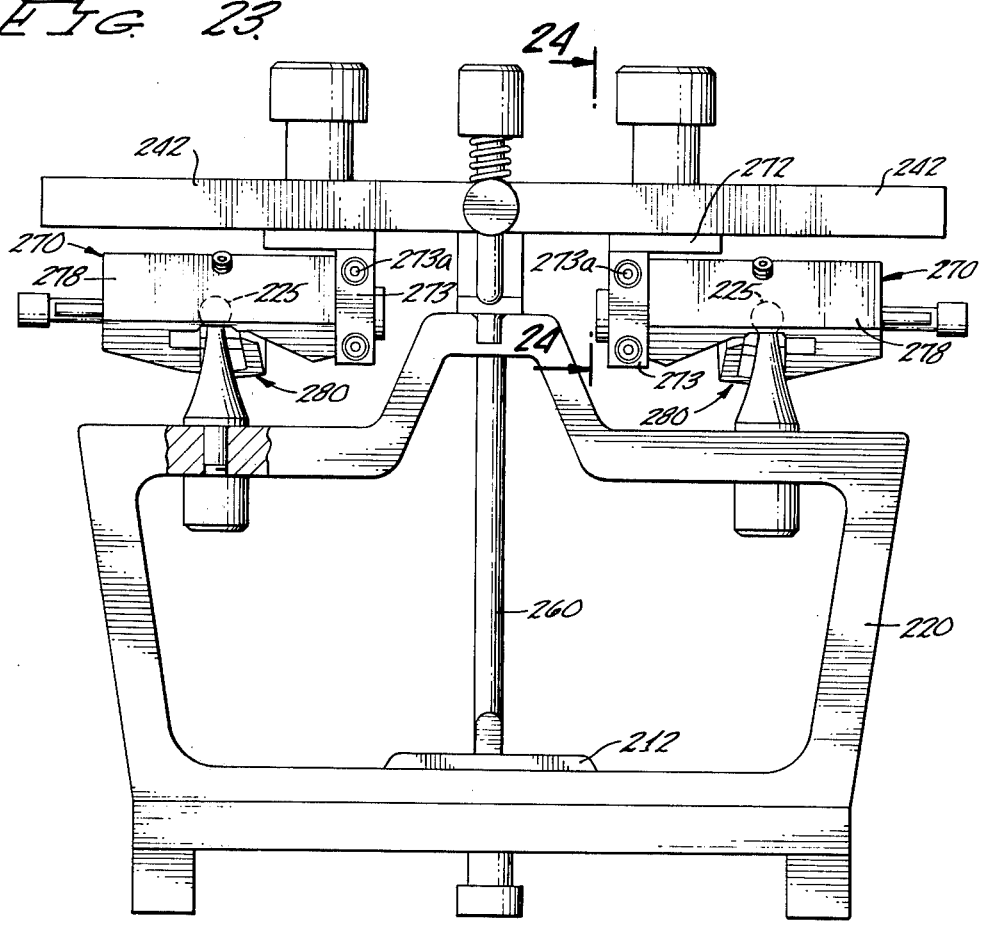
FIG. 23 is a rear elevational view of the instrument of FIG. 22.

With the apparatus and methods described above, jaw movements are readily measured. Such information is useful for properly adjusting dental articulators which are utilized to simulate jaw movements. That is, the side shift, immediate and full, and the slope of the upper wall of the guide boxes used for controlling articulator movement can be set. For example, referring to FIGS. 22 and 23, there is shown a dental articulator or jaw movement simulator including a lower frame or assembly A and an upper frame or assembly B which respectively represent the lower and upper jaws of a human for simulating jaw movement. In the position illustrated, the upper assembly B can be pivoted on the lower assembly A which is reverse to the human mandible or lower jaw which slides with respect to the maxilla or upper jaw, however the relative motion between the two frames is the same.

The lower assembly A includes a generally T-shaped base member 210 having a forward arm 211 and an incisal pin rest pad 212 mounted thereon. Mounted on top of the rear of the base member 210 is a vertical frame member 220 supporting a pair of spaced spherical styluses 225 which represent the simulated horizontal or hinge axis of the condyles of a human. A screw 231 projects upward through an opening in the arm 211 for attaching a dental mounting plate schematically illustrated at 232.

The upper assembly B of the articulator includes a T-shaped upper frame member 240 having lateral slotways 245 in its transverse arm 242. Attached to the forward end of the forward arm 241 is an incisal rest pin 260 which has its lower end supported on the upper surface of the rest pad 212 on the lower assembly. A horizontal flag 264 used to indicate the horizontal plane of reference is attached to the forward end of the arm 241 immediately to the rear of the incisal pin 260. The undersurface of theis flag forms a horizontal plane with the hinge axis through the styluses 225 when the guide housings are at centric relation position. The forward arm 241 is adapted to receive a mounting plate for a maxillary dental cast schematically illustrated at 252 in FIG. 22.

Figure 24:
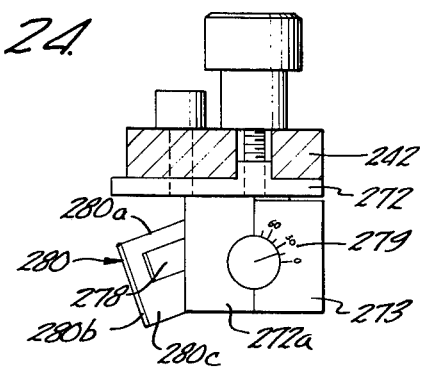
FIG. 24 is a cross-sectional view on the line 24—24 of FIG. 23 illustrating the adjustable mounting for one of the guide boxes.
Figure 25:
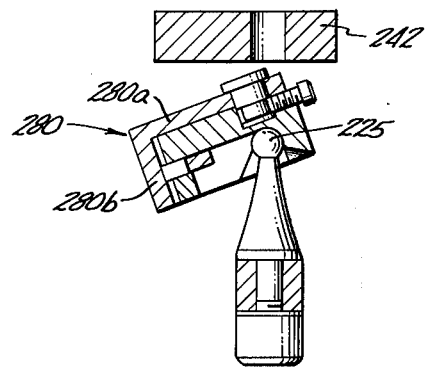
FIG. 25 is a cross-sectional view on the line 25—25 of FIG. 23 illustrating the adjustable mounting of the medial wall of the guide box.
Figure 26:
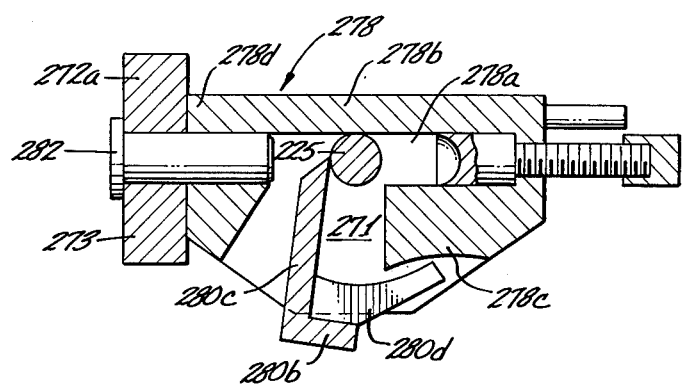
FIG. 26 is a cross-sectional view on line 26—26 of FIG. 25 illustrating the shape of the guide box.

Attached to the outer arms 242 of the upper frame assembly are a pair of guide assemblies 270 which cooperate with the styluses 225 of the lower frame. Attached beneath the arm 242 for each guide assembly is a mounting plate 272 having a trunion portion 272a (FIG. 24) to which is attached a mating trunion member 273 by suitable fastening elements 273a seen in FIG. 23. Each guide assembly 270 includes a pair of irregular five wall guide boxes 271 whose walls are formed by a primary guide housing 278 and a secondary member or housing 280. Referring to FIG. 26 as well as to FIGS. 22–25, the primary guide housing 278 has a generally flat upper wall 278a, a generally flat rear wall 278b, and a generally flat outer wall 278c. The primary guide housing 278 also includes a mounting end 278d having a retained cup-end shaft or pin 282 which is gripped by the trunions 272a and 273. The primary guide housing 278 is joined to the pin 282 to act as one piece, and hence the entire guide housing can be rotated horizontally as desired with the pin 282 and clamped in this position by means of the fastener 273a. An angular scale 279 is formed on the trunion 273 as shown in FIG. 24 to indicate the angular orientation of the guide housing 278 to the horizontal plane. Thus the general slope of the protrusive path 94 shown in FIG. 20 is used to set the angle of the guide housing 278, the information being measured by the protractor 96 or shown on the electronic readout 106 and 107 of FIG. 21.

Figure 27:
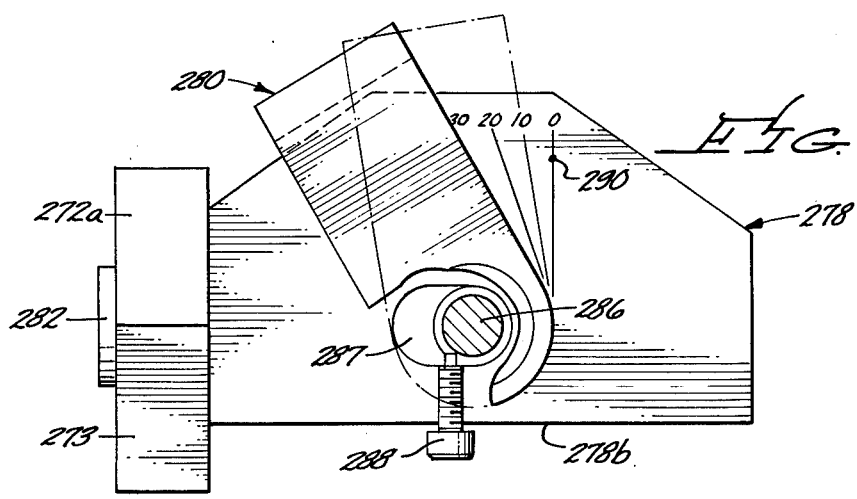
FIG. 27 is a top view of a guide box showing the adjustability of the medial wall.

The secondary guide housing 280 is an irregularly shaped element preferably formed as an integral piece which fits onto the primary housing 278. The secondary housing 280 includes a horizontally flat upper support arm 280a, (when viewed in the orientation of FIGS. 22 and 25) a vertical wall 280b, a flat vertically orientated but horizontally extending wall 280c attached to the vertical wall 280b, and a generally flat, curved, finger-like front guide wall 280d extending outwardly from the walls 280b and 280c. The flat support arm 280a is mounted on the primary guide housing with a pivot pin 286 by means of a set screw or other suitable means not shown. Referring to FIG. 27, the opening 287 through which the pin 286 extends is elongated laterally so that the pin 286 carrying the inner guide wall 280c may be moved inwardly a small amount, such as about 2 millimeters. An adjustment of this type for both right and left guides thus may provide a total horizontal side shift of 4 millimeters. A set screw 288 extending through the rear wall 278b of the primary guide housing 278 engages either one side or the other of the pivot pin 286 to laterally fix the pin 286 and the secondary guide housing 280 and also to prevent rotation once the desired angular setting of the inner wall 280c has been made. The vertical support wall 280b of the secondary housing 280 extends adjacent the forward edge of the housing 278 and the internal surface of the horizontally extending vertically oriented wall 280c forms the inner or medial surface for the guide box 71.

Thus, the side shift information obtained as discussed above in connection with FIGS. 7–9 is used to set the lateral position of the pin 286 in the slot 287. Structure to provide fine degrees of adjustment may be utilized if desired. The angle of the member 280, and thus the angle of the medial wall 280c of the guide box is set by using side shift measurement (Z axis) and forward movement information (X axis) during a chewing operation. Referring to FIG. 27, the X axis information is measured in the forward direction on the O angle line, and the Z axis information is measured perpendicular to the O angle line. In the case of the electronic measuring means, the X and Z readings are conveniently available at any point, and can be scaled off on the guide housing at any point in setting the member 280. In the case of the mechanical arrangement, the maximum or full side shift, as determined above in reference to FIGS. 7–9, has been found to be near where the paths P and L of FIG. 20 stop moving downwardly or in the Y direction. The full chewing side shift is typically obtained at about the ten millimeter mark on the X axis. Thus a mark 290 may be conveniently formed on the zero angle line on the upper side of the guide housing 278 ten millimeters from the hinge axis in centric position through the center of the pin 286, as shown in FIG. 27, and the full side shift measurement utilized at that point to position the member 280. A scale for full side shift may be marked on the member 280 if desired.

In some articulators available, the slope of the upper surface 278a of the guide box adjacent the medial wall 280c can be separately adjusted. Information for this is obtained from the slope of the curve L in FIG. 20 or from the electronic readout on the XY axes while in side chewing position. Also some articulators can make adjustments for backlash B and this information is available from the grid plate in FIG. 20 or from the electronic readout.

b. Preformed Analogue Guide Blocks

Figures 28, 29:
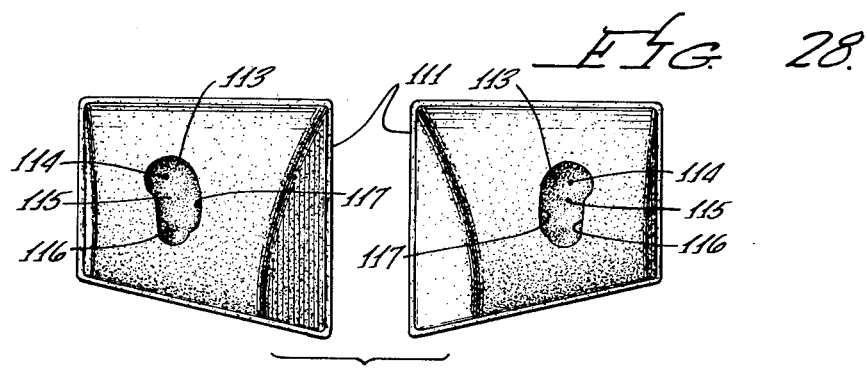
FIG. 28 is a perspective view of a set of analogue blocks having openings for guiding an aritculator lower frame to simulate a mandibular movement.
FIG. 29 is a chart illustrating use of preformed standardized analogue blocks.

The information obtained may also be utilized for preparing or selecting openings in analogue guide blocks which when used with an articulator in place of the guide boxes 271 of the simulator in FIGS. 22–27, more precisely duplicate or simulate the joint movements. One such set of blocks 111 having openings 113 is shown in FIG. 28, by way of example.

For convenience of comparison, the guide blocks 111 are shown oriented similar to the guide boxes 271 of the simulator shown in FIG. 26. While the guide boxes are straight line and have generally planar walls, the walls of the guide blocks are usually curvilinear and thus more accurate. The points 114 in FIG. 28 mark the location of the styluses 225 of FIG. 26 when positioned in the five-sided irregularly shaped guide block pathways or openings 113 in centric relation. The upper wall 115 of the guide blocks corresponds to the wall 278a of the guide boxes 271, while the lateral wall 116 and medial wall 117 correspond to the guide box walls 278c and 280c respectively.

As mentioned above in connection with the earlier Lee patent, the procedure of machining a special set of analogue blocks for each patient is somewhat expensive. Such blocks have now been made on a relatively large number of patients and the characteristics of these blocks have been analyzed. This analysis discloses that most of the joint movements may be classified into a relatively small number of categories. For example, by classifying the pathways of the analogue blocks into just three variations of immediate side shift and three variations of the slope of the protrusive curve, nine relatively broad categories are created. FIG. 29 is a table introducing two other variables for a total of 36 categories. The first column indicates immediate side shift of zero, one millimeter and two millimeters. The second column indicates the slope of the protrusive curve at a selected location in 15° increments of 30°, 45° and 60°. Column 3 lists the slope of the lateral or border path as 45° or 60°. Column 4 specifies the full side shift in 5 or 7 millimeters at 10 millimeters forward from centric, which determines the angles of the medial wall.

By selecting these broad categories, analogue blocks having such characteristics can be prepared in large quantities. A main advantage of this arrangement being that if only certain standardized sizes are utilized, the blocks can be made by inexpensive manufacturing techniques such as molding. Thus, when the jaw movement parameters of a patient are measured it is a simple matter to select a set of blocks which most closely fit these measured parameters. The cost of the blocks are such that possibly individual dentists can afford to maintain a supply. Thus the desired set of blocks can be simply selected and mounted in an articulator to quickly enable the patient's jaw movements to be simulated.

Naturally for those patient's having unusual jaw movements such that they do not fall into the standardized categories, the more precise technique of making a custom set of analogue blocks may be employed if desired. Also, it should be understood that the number of standardized categories can be increased to improve precision. For example, further breakdowns in any of the variables in the chart of FIG. 29 can be employed. Introducing additional variables or further refinements of the increments would eventually made the selection somewhat difficult for an individual. Thus, the information could be stored in a computer and the computer programmed to receive the patient's jaw measurements and made the proper selection of analogue blocks amongst the stardardized categories. With the electronic monitoring means for measuring jaw movements, the number of classifications is almost infinite, but the number of standard sizes would have to be kept at a realistic level to maintain the practicality of the system. If the computer could not match a specific patient's jaw measurements to any of the stock selections it would indicate that this individual's movements were significantly different from all of the others. In this case this patient should be recorded with the Lee method in the above-identified patent and other related Lee patents.

What is claimed is:

1. Dental apparatus for analyzing or recording jaw movements comprising:
   an upper frame having two thin flat rigid recording plates, mounted to be positioned one on either side of a patient's head perpendicular to the horizontal axis of the patient's temporomandibular joints, said plates having a grid formed on their outer surface;
   a lower frame affixed to the patient's mandible, said mandibular frame having a pair of side arms one on either side extending alongside but spaced from the patient's face, and means mounted on each of said side arms extending inwardly to engage said grids on the upper recording plates to monitor or record mandibular movements on said grid; and
   means removably mounted on said upper frame for providing on said grid a reference line in a plane through said axis and a third point on the upper frame aligned with a point on the patient's face or nose, whereby measurements of said movements may be made in relation to said reference line.

2. The apparatus of claim 1 wherein said upper frame includes a transverse rod to be supported on a patient and side arms mounted perpendicular to the transverse rod in a manner such that they cannot be moved out of perpendicular relation.

3. The apparatus of claim 1 including separator means mounted on said mandibular frame for extending into the patient's mouth to separate the mandible and maxilla during said mandibular movements.

4. The apparatus of claim 3 wherein said separator means is movably mounted on said mandibular frame in a manner such that it can be moved into the patient's mouth when jaw separation is desired and moved out of the mouth when desired, while the mandibular frame remains affixed to the mandible.

5. The apparatus of claim 4 wherein said mandibular frame includes a transverse rod on which said mandibular side arms are mounted, and said separator means is pivotally mounted on said rod.

6. The apparatus of claim 3 including clutch means mounted on said mandibular frame for securing the mandibular frame to the patient's mandible, and wherein said separator means is supported on said clutch means.

7. The apparatus of claim 1 wherein said means engaging said grids comprises a pin which is movably mounted on each of said mandibular side arms to be movable toward and away from the side arm, and a marker movably mounted on each of the pins movable by movement of the side arms relative to said pins as a measure of the lateral movement of a patient's mandible.

8. The apparatus of claim 1 wherein the means engaging said grids comprises a stylus for marking a path on said grid during said mandibular movement.

9. In dental apparatus for analyzing and recording jaw movements, including a mandibular frame comprising:
   a transverse rod;
   clutch means for affixing the transverse rod to the patient's mandible;
   a pair of side arms affixed to the transverse rod to extend rearwardly along the patient's face; and
   an element mounted on each of said arms and extending inwardly to engage a point aligned with the terminal hinge axis position of the patient's mandible, said elements being movably mounted on said arms, a marker on each of said elements for indicating movement of the arms toward and away from said hinge axis points as a measure of the side movement of the patient's mandible.

10. The apparatus of claim 9 wherein said markers grip the elements but are also slidable when adequate force is applied.

11. The apparatus of claim 10 wherein said elements are axis pins slidably mounted on said arms and said markers comprise small rings made of a material such as plastic which will grip the elements but yet will slide, when adequate force is applied.

12. The apparatus of claim 9 including
   a holder mounted on each of said side arms, the axis of each holder extending perpendicular to the side arms said elements being slidably mounted on the holders, and means mounted on each of said holders for selectively gripping said elements.

13. The apparatus of claim 12 wherein said element includes a writing element on its innermost end for writing on a recording surface supported on a maxillary frame.

14. Apparatus for recording jaw movements comprising:
   an upper frame having two plate-like members for positioning one on either side of the patient's head overlying the patient's temporomandibular joints;
   a lower frame for affixing to the patient's mandible including side arms positioned outwardly from said members;
   a probe supported on each side arm extending towards said members with the probe tips positioned adjacent said members; and means connected to said probes and said members for electronically monitoring movement of said probes relative to said members including digital readouts to provide numerical information regarding the patient's mandibular movement useful for setting or preparing a dental articulator to simulate a patient's movement.

15. The apparatus of claim 14 wherein said members include means for sensing movement of the probe.

16. The apparatus of claim 14 including means for biasing said probes against said members, and said monitoring means include means for sensing lateral movement of said lower frame relative to said probe.

17. A method of recording the angle or path of mandibular axis motion comprising the steps of:
   vertically supporting a pair of record plates, one on each side of a patient's face overlying the area of hinge axis motion of the patient's mandible;
   affixing a mandibular frame to the patient's mandible, said frame having styluses affixed to the side arms of the frame and engaging said record plates;
   moving the patient's mandible while maintaining the styluses in contact with the plates to obtain a path of such movement on the record plates; and
   providing on said plates a reference line which is in a plane through said hinge axis and a reference point on the patient's face or nose, whereby the characteristics of said path with respect to said reference line may be directly measured and used for preparing a dental articulator to simulate the patient's jaw movements.

18. The method of claim 17 wherein said record plate includes a thin sheet removably mounted on the exterior of the plate, and said stylus is a writing implement which will write on said sheet.

19. A method of measuring mandibular side movements comprising:
   affixing a frame to a patient's mandible;
   affixing a frame to the patient's maxilla;
   affixing to one of said frames a rigid surface overlying the patient's temporomandibular joints;
   affixing to the other of said frames a pin generally perpendicular to and in engagement with said surface, one of said surface and said pin being slidably mounted to its frame;
   shifting the mandible sideways in the direction to cause displacement between said one slidably mounted element and its supporting frame; and
   measuring the displacement to obtain a measure of the sideways shifting of the mandible.

20. The method of claim 19 wherein said displacement is measured electronically to provide a digital readout.

21. A method of measuring mandibular side movements comprising:
   affixing to a patient's mandible a frame having a side arm extending along the side of a patient's face;
   slidably mounting a horizontal pin on said arm, with the pin extending perpendicular to the arm towards the patient's face;
   positioning the pin over tnhe patient's temporomandibular joint in engagement with a fixed rigid surface overlying said joint;
   shifting the mandible sideways in the direction to cause the side arm to be displaced on said pin; and
   measuring the displacement of said arm with relation to said pin.

22. The method of claim 21 including axially locking the pin while it is in contact with said surface, positioning a marker on said pin in engagement with a reference surface on said frame, unlocking the pin and then moving the mandible sideways so that the side arm is moved towards said fixed rigid surface and the displacement of the side arm relative to the pin is conveniently represented by the distance between the marker and said reference surface on the frame.

23. The method of claim 21 wherein in said pin positioning step the pin is axially aligned with the hinge axis of said joint with the mandible in centric position.

24. A method of recording the protrusive angle or curve of mandibular axis motion comprising the steps of:
   vertically supporting a record plate on the side of a patient's face overlying the hinge axis of the patient;
   supporting a stylus with its tip adjacent said record plate;
   affixing a mandibular frame to the patient's mandible with one of said plate and said stylus affixed to said frame and the other of said plate and stylus being fixed with respect to the patient's maxilla; and
   electronically monitoring the relative movement of said stylus and said plate while moving the patient's mandible to thereby produce on digital readouts information of the movement useful for preparing a dental articulator to simulate a patient's jaw movement or for other dental diagnostic purposes.

25. The method of claim 24 including the step of establishing a plane of reference through said hinge axis in centric position and a point on the patient's nose so that the curve of mandibular movement may be measured with respect to said reference plane.

26. The method of claim 25 including the step of positioning a flat reference plane tool on a nose pointer mounted on a frame mounted on the patient's maxilla and aligning the tool with said hinge axis as located by said stylus.

27. Dental apparatus comprising:
   a maxillary frame having a transverse rod to be supported on a patient's nose, a pair of side arms attached to the transverse rod to be supported on the patient's ears, a pair of recording plates attached to the side arms to overlie the patient's temporomandiublar joints, and a pointer mounted on said transverse rod to engage the patient's nose; and
   a reference plane tool to fit over the maxillary frame having a pair of side legs to engage the recording plates, and an element attached to the tool with a dimple therein for receiving said nose pointer, said dimple being in the same plane as the upper surfaces of said tool legs.

28. A tool for use with a maxillary recording frame comprising:
   a pair of L-shaped members having flat upper surfaces;
   one of said members having a recess formed in one leg for receiving a leg of the other member so that with the legs overlapping the members together form a U-shaped, the depth of said recess being equal to the thickness of the leg received therein so that the upper surfaces of the two members are in a single plane, the width of the U-shaped space between the members being adjustable by means of the recess and leg therein; and a point receiving element attached to said tool and extending outwardly from the tool, the point receiving element having a dimple in an edge surface for receiving a nose pointer of a maxillary recording frame.

29. A method of simulating jaw movements comprising the steps of:
measuring specified parameters of a patient's lower jaw movements;
selecting from a preformed supply of analogue guide blocks having openings formed therein of standardized sizes, classified on the basis of said specified parameters, the set of blocks best fitting said patient's jaw movement parameters the opening in each of said blocks being adapted to receive a spherical stylus on a dental articulator, said opening having an upper wall and walls extending around the opening including an outer or lateral side wall, an inner or medial wall, a rear wall adjacent a centric position point, and a forward wall; and
mounting the selected analogue blocks in a dental articulator to receive the articulator styluses and simulate the patient's jaw movements.

30. The method of claim 29 wherein one of said specified parameters is the jaw side shift from centric position permitted by the side walls of said opening.

31. The method of claim 30 wherein said side shift is the immediate or direct initial lateral jaw movement.

32. The method of claim 31 wherein another one of said specified parameters is the slope of a protrusive jaw movement at a specified location.

33. The method of claim 32 wherein another of said parameters is the full side shift permitted at a specified location forward from the centric point.

34. The method of claim 29 wherein said supply of blocks is made by molding techniques.

* * * * *